United States Patent [19]
Canard et al.

[11] Patent Number: 6,001,566
[45] Date of Patent: *Dec. 14, 1999

[54] DNA POLYMERASE HAVING 3'-INTRINSIC EDITING ACTIVITY

[75] Inventors: Bruno Canard, Cambridge, Mass.; Gregor Sagner, Penzberg, Germany

[73] Assignee: Roche Diagnostics GmbH, Mannheim, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/655,777

[22] Filed: May 31, 1996

[30] Foreign Application Priority Data

Jun. 1, 1995 [EP] European Pat. Off. .............. 95108369

[51] Int. Cl.$^6$ .............................. C12Q 1/68; C07H 21/04; C12P 19/34
[52] U.S. Cl. ............................ 435/6; 435/91.1; 435/91.5; 435/183; 536/23.1
[58] Field of Search .............................. 435/91.1, 6, 91.5, 435/183; 436/94; 536/23.1

[56] References Cited

PUBLICATIONS

Canard et al., DNA polymerase fluorescent substrates with reversible 3' tags, Gene, vol. 148, pp. 1–6, Oct. 1994.

Murray et al., The determination of the sequences present in the shadow bands of a dinucleotide repeat PCR, Nucleic Acids Research, vol. 21(10), pp. 2395–2398, 1993.

*Primary Examiner*—Nancy Degen
*Assistant Examiner*—Andrew Wang
*Attorney, Agent, or Firm*—Nikaido Marmelstein Murray & Oram, LLP.

[57] ABSTRACT

The invention is directed to the use of RNA or DNA polymerases having 3'-intrinsic editing activity (3'-IEA) in the presence or absence of a deactivating agent to remove a protecting group from the 3'-position of oligo- polyribo- or deoxyribonnucleotides. The use is connected with the incorporation of dNTPs into DNA templates in order to determine the concentration and/or sequence of said templates. In particular the use is concerned with an improved non gel-based sequencing method.

27 Claims, 7 Drawing Sheets

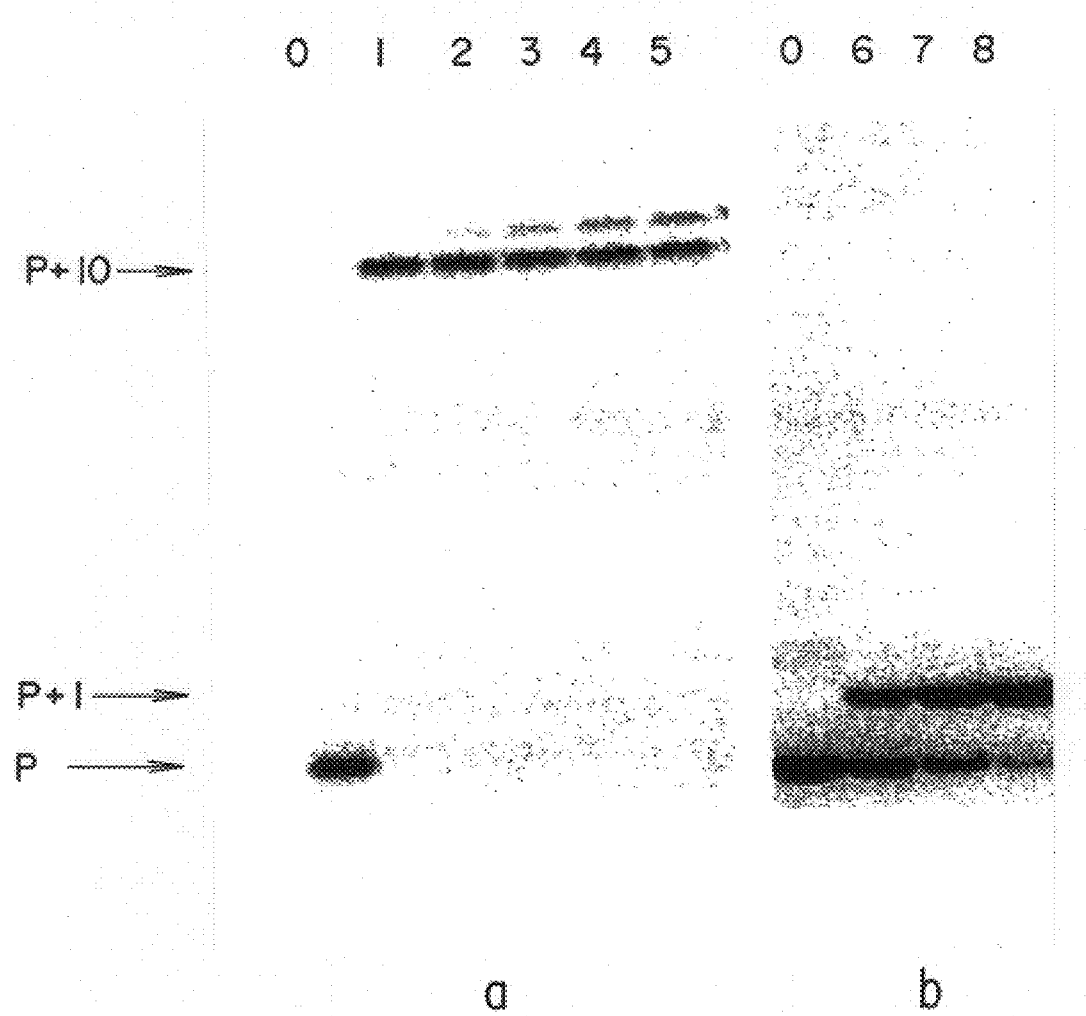

DNA POLYMERASE HAVING 3'-INTRINSIC EDITING ACTIVITY

The invention is directed to the use of DNA or RNA polymerases having 3'-intrinsic editing activity (3'-IEA) in the presence or absence of a deactivating agent to remove a protecting group from the 3'-position of oligo- or polyribo- or desoxyribonucleotides. The use is particularly concerned with an improved non gel-based sequencing method.

Modern molecular genetics is currently yielding important advances in understanding complex biological processes and pathologies such as cancer or hereditary diseases. This has been made possible mainly by the development in the late '70s of nucleotide sequencing techniques (Sanger. 1977. Maxam and Gilbert, 1977). These classical methods are still in use in their original form in most laboratories around the world. Despite its wide acceptance as the method of choice, the Sanger's dideoxy method has not been completely automated yet, mainly due to the gel electrophoresis step. Consequently this batch-step has been improved in terms of speed and number of processed samples, but attempts are currently underway to search for alternate method that would circumvent these obvious limitations. These efforts have not been greatly rewarding, and only new emerging concepts and projects have appeared recently, such as sequencing by hybridization (Strezoska et al, 1991) or scanning tunneling microscopy (Driscoll et al, 1990).

With such ideas in mind, several teams have proposed a new approach that would take advantage of the enzymatic power of the Sanger's dideoxy method, but without generating a complex mixture of products subsequently analysed by polyacryiamide gel electrophoresis (Tsien 1991, Gibbs et al 1993, Canard and Sarfati, 1993). This new approach relies on a single-base addition in a growing DNA strand complementary to the nucleotide sequence to be determined. Each added base is identified in a stepwise manner, and the unknown sequence is deduced in real-time during a fully automatable scheme. In order to control addition of one and only one base by a DNA polymerase, special nucleotide 5'-tri phosphates of the four bases ATGC have to be designed in such a way that they are still good DNA polymerase substrates, can be easily distinguished one from another, and can act either as chain-terminators or once incorporated as new 3'-primer for addition of the next base to be identified.

Chemical protection of the 3'-hydroxyl of such substrates would give them these desired properties as long as once one has been incorporated, their 3'-blocked hydroxyl could be deprotected to restore a functional 3'-end. In this manner, the 3'-protection acts as a tag of each of the four bases ATGC, and its identification means the identification of the nucleobase corresponding to the DNA template using standard rules of bases pairing, and thus provides a very easy way for determining a nucleotide sequence once this process is efficiently cycled. Many 3'-modified-2'-deoxynucleotide 5'-tri phosphates have been synthesized and shown to be substrates for DNA polymerases (Kornberg, 1980, Tabor and Richardson, 1989, Kraevsky, 1987, Canard & Sarfati, 1994a), and this leaves little doubt about the feasibility of the incorporation reaction under reasonable time. Likewise, fluorimetric detection of nucleotides or elongated DNAs with fluorescently labelled bases is currently used on standard protocols of semi-automated sequencing machines (Venter et al, 1992), as well as envisaged on single fluorescent molecules released in an 3'-exonuclease-driven reaction (Davis et al, 1991). This makes incorporation and detection problems already tractable at the level of development and automation.

This is clearly not the case for deprotection which thus remains the key step. The 3'-position has to be protected in such a way that it is completely stable under standard incorporation conditions to avoid formation of unwanted minute concentration of unprotected nucleoside 5'-triphosphate, but is easily deprotected under other mild conditions compatible with DNA chemical and duplex stability. Gibbs et al, 1994, have designed such thymidine nucleotide substrate with a 3'-spacer arm which is light sensitive and thus restores a 3'-hydroxyl end upon UV irradiation. However, this requires sophisticated and difficult chemistry to be applied to the three remaining bases AGC, leaves few flexibility in the spacer arm-design and thus the corresponding tag, and no data exists concerning the use of other DNA poles than Bst DNA pole I (Gibbs et al, 1994).

Canard and Sarfati (1993) have designed new 3'-modified 2' deoxynucleotides that are indirectly and immediately deprotected under neutral conditions at room temperature. These authors have also presented data on enzymatic deprotection using esterase-like enzymes able to hydrolyse 3'-esters, at a reduced rate, though (Canard and Sarfati, 1994a).

Enzymatic deprotection has all the required properties to be fully integrated in such a sequencing process, except that it must be kinetically attractive, that is, deprotection ideally should proceed within seconds.

During the search for ideal incorporation conditions, it was found that most DNA polymerases could be used to deprotect the 3'-blocked end of the terminated DNA, circumventing the tedious search for an appropriate 3'-deblocking enzyme or method (Canard and Safarti, 1994 a, b). However, this general property of DNA polymerases renders completely invalid in non gel-based sequencing schemes as described in Tsien, 1991, or the like.

Such non gel-based sequencing, whereby a complementary strand is prepared stepwise by the mean of a DNA-polymerase, and no time-consuming gel electrophoreses are needed afterwards, have essential advantages over the classical methods of, e.g., Sanger (WO 91/06678, WO 93/05183, DE 4141 178, U.S. Pat. No. 5,302,509, FR 93 03 538). A 3'-modified nucleotide (DNA chain terminators) is presented as a DNA-polymerase substrate. However, removing of the group, introduced to the 3'-end of the DNA strand (3'-tag), must be carried out in a second step. Chemical, photochemical and enzymatic methods are usually applied in this regard.

The main problem to be resolved according to the present invention is, therefore, to overcome the above mentioned disadvantages.

This problem is resolved by the present invention and is directed to the use of a DNA-polymerase having 3'-intrinsic editing activity (3'-IEA) as a tool in several molecular biology techniques, in particular in non gel-based sequencing techniques. The 3'-IEA allows the use of 3'-modified DNA polymerase substrates that are not DNA chain terminators. Since the 3'-tag is removed by the DNA polymerase during addition of the next nucleotide, the initial 3'-modified nucleotide is a false chain terminator that has its 3'-position converted to a functional 3'-end capable to act as a primer for the next nucleotide. The key fact which is at the basis of the present invention is that the 3'-tag is released by the DNA polymerase itself concomitantly to the addition of the next correct nucleotide. Hence, the 3'-tag released is indicative of which nucleotide has been inserted, but also indicative of which next nucleotide has provoked the release of the tag. The fact that the DNA polymerase is able to release a 3'-tag upon insertion of a 3'-tagged nucleotide followed by addition of a given classical nucleotide is thus informative about two consecutive nucleobases on an unknown DNA strand. This can be used to remove a 3'-tag specific of an inserted nucleotide in a non gel-based sequencing scheme as described by Tsien. 1991, Gibbs et al, 1991, Canard and Safarti, 1993. In this case, the 3'-IEA is key to efficiency perform the deprotection step and subsequently identify which base has been inserted. It is also of interest to note that polymerization of a mixture of three out of the four classical nucleotides and the fourth 3'-tagged nucleotide, on a primed DNA in the presence of a DNA polymerase having 3'-IEA will proceed normally, but the 3'-tag will be released in the medium as soon as the nucleotide carrying it is incorporated into DNA. Hence, the presence of the free tag in the medium will be indicative that polymerization has occurred. This is of particular interest to quickly check if polymerization has occurred in a given reaction mixture (such as PCR). Preferably, the tag will be easily identified in its free form compared to its 3'-attached form.

Typical DNA polymerase substrates according to the present invention are compounds of general formula (I):

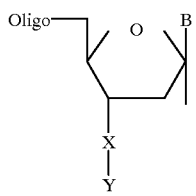

(I)

wherein X is a bifunctional linkage group, Y is a residue providing an activated group and residue B is a purine, pyrimidine, deazapurine, deazapyrimidine or analogues thereof, preferable compounds wherein X is an oxygen, sulfur or a —NH-group and Y is a —C(O)R, —CH$_2$—R, —C(S)NH—R or —C(O)NH—R group wherein R is a hapten, a dye or a chromophore as, e.g., a fluorescent chromophore or a branched or unbranched alkyl group consisting of at least one atom.

In particular 2'-deoxy 3'-esterified nucleotide 5'-triphosphates act as substrates for several DNA polymerases in a simple standing start assay using the cognate nucleotide alone. However, when a mixture of the four 3'-esterified deoxynucleotides was used, more than one addition product was observed with E. coli DNA polymerase I large fragment and T7 DNA polymerase. This was not the case for Taq DNA polymerase nor several other thermophilic enzymes, suggesting that readthrough was not due to a minute concentration of 3'-unprotected deoxynucleotides. Optimal incorporation levels using Taq DNA polymerase are surprisingly achieved at temperatures between 37° C. and 45° C., far below the known optimum temperature of 72° C. for Taq DNA polymerase activity. However, there was no difference in product pattern when a cloned versus native thermophilic enzyme was used, ruling out a possible contamination of the cloned product by E. coli DNA polymerases. The removal of the 3'-ester was also consistently independent of the presence or absence of a 3' to 5' exonuclease activity often associated with DNA polymerase molecules, as exemplified by the use of genetically engineered T7 DNA polymerase (Sequenase) lacking such proofreading activity. When 3'-esterified nucleotides were pre-incubated with T7 DNA polymerase in the absence of DNA, the enzyme subsequently heat-inactivated and the mixture incubated with a DNA template/primer and Taq DNA polymerase, a single addition product was observed as before, indicating that the 3'-esters were not hydrolyzed prior to incorporation.

Another object of the invention to use DNA polymerases having 3'-IEA is concerned with the quantity of free tag released in the medium which is stoechiometric to the quantity of its carrier nucleobase that has been inserted in the growing DNA strand. This is of particular interest in determining the number of repeats of a given base, a given dinucleotide, a given tri-nucleotide, or any given repeated sequence that contains only three out of the four bases ATGC. Then, in such an assay, the quantity of tag released in the medium when polymerization occurs through a stretch of a repeated motif is directly proportional to the number of repetition of the said motif. This is of particular importance when the number of repeats in a DNA sequence is correlated with the onset or full expression of a hereditary disease, such as, for example, the fragile X syndrome (Fu et al, 1991), or other diseases involving similar molecular defects.

Another aspect of this invention is that it identifies a position in modified nucleotides (or nucleotides analogues) that can be modified chemically without altering incorporation properties of these substrates. Hence, this 3'-position can be used to chemically attach substituents giving to the nucleotide analog different properties than the starting 3'-hydroxyl nucleotide analog. It is then possible to alter physical properties of nucleotide analogs toward increased hydrophobicity, hydrophilicity, polarity, or else, without altering their incorporation properties by the polymerase. This is of particular importance in antiviral chemistry where the 5'-tri phosphate form of a nucleotide analog can be a potent inhibitor of virally encoded reverse transcriptase in vitro, but be inefficient in vivo because the charged 5'-mono, di, or tri phosphate prevents delivery inside the living cell due to its inability to cross the apolar cytoplasmic membrane. A lipophilic ester in the 3'-position greatly changes the hydrophobic properties of such a 5'-monophosphate nucleotide analog, allowing facile entry inside the cell, and thus by-pass the need of a specific 5'-kinase reaction on the nucleotide analog. This is of great clinical relevance as virus strains can become drug-resistant by loss of their kinase gene. In a more general manner attaching a substituent which has lipophilic properties in the 3'-position of a nucleotide allows to compensate for a hydrophilic or polar character brought by a 5'-mono, di or triphosphate. Once inside the cell this 3'-lipophilic nucleotide 5'-mono, di or triphosphate can be converted to the 5'-triphosphate form— if required—by cellular kinases, and incorporated into DNA. If the 3'-lipophilic nucleotide carries a modified base, because of the 3'-IEA, this modified nucleotide will be incorporated into the cell's DNA together with its modified base, leaving the former 3'-lipophilic substituent in a free form, that is, non-covalently bound to the DNA, thanks to the 3'-IEA. It is also obvious for one skilled in the art that this can be used to deliver a compound in the cell that would not be easily introduced alone inside the cell.

BRIEF DESCRIPTION OF THE DRAWING

Legends

FIG. 2 End-labelled primer extension and gel assay using 3'-ant-dNTPs and DNA polymerases as, 3'-ant-dNTPs were as described in Gene 148 (1994), 1–16 by Canard and Sarfati. a, 3'-esteried-dNTPs (400 μM) were incubated with primer/template and Sequenase for 0, 1, 2, 3, 4, 5 min (lanes 0, 1, 2, 3, 4, 5 respectively), b, The same primer/template and 3'-esterified nucleotides (2 mM) were used with Taq DNA polymerase for 0, 5, 10, 15 min (lanes 0, 6, 7, 8 respectively). P: prirner (21-mer). Samples were run through a 15% denaturing polyacrylamide gel which was autoradiographed.

Panel b) shows how this sequencing scheme can be adapted to a very large number of DNA samples immobilized on a solid support (S. Fodor, Science 264 (1994), 1400) and the incorporation scores recorded by an image analysis system (CCD camera).

Figure 3A:
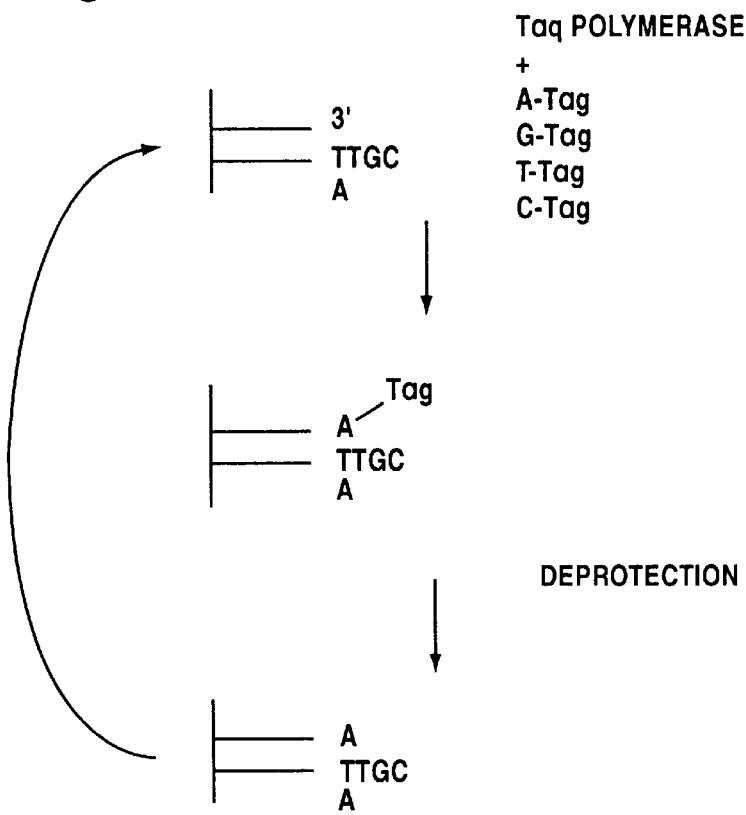
FIG. 3 Panel a) shows how to use a DNA polymerase (5 units) and four 3'-tagged nucleotides-5'-triphosphate (1 mM) in a non gel based sequencing scheme to determine the nucleotide of am unknown DNA stand (2 picomoles) which is immobilized on a solid support (Dynabead M-280, Dynal).
Figure 3B:
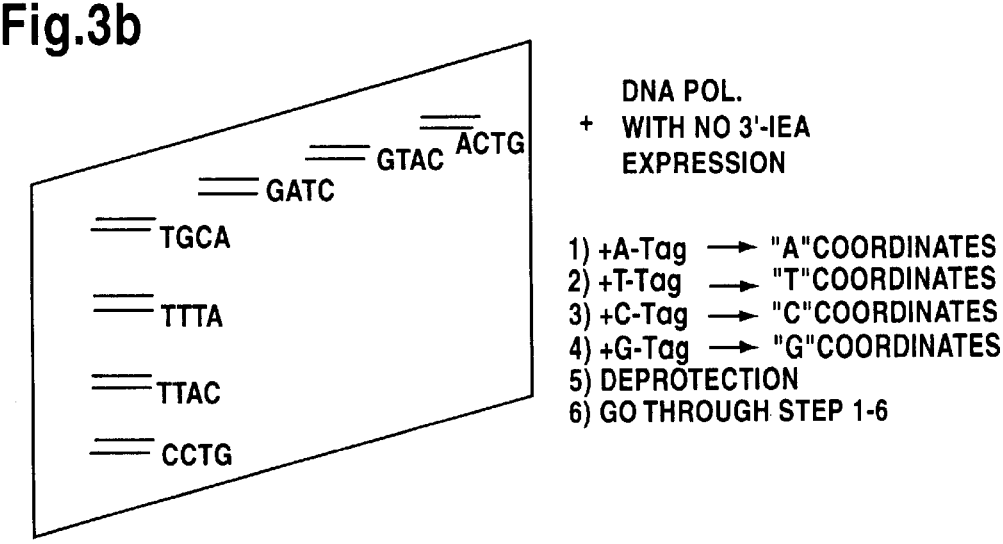

FIG. 4 Panel a) shows that Taq polymerase is able to perform what is depicted in FIG. 3, but under classical reaction conditions (72° C., ph 8.3, 1–5 mM $Mg^{2+}$) in order to fully inhibit 3'-IEA of Taq polymerase (30°–40° C., pH 7,5, 1 mM $Mn^{2+}$, 5 mM citrate, 1 mM of each 3'-tagged nucleotides).

Panel b) illustates a way of assaying the concentration of the double-standed product when the PCR is completed. A mixture of ree dNTs and a 3'-tagged dNTP is added to the PCR, and only on PCR cycle is performed under the temperature of the DNA polymerase's optimum activity.

Figure 5:
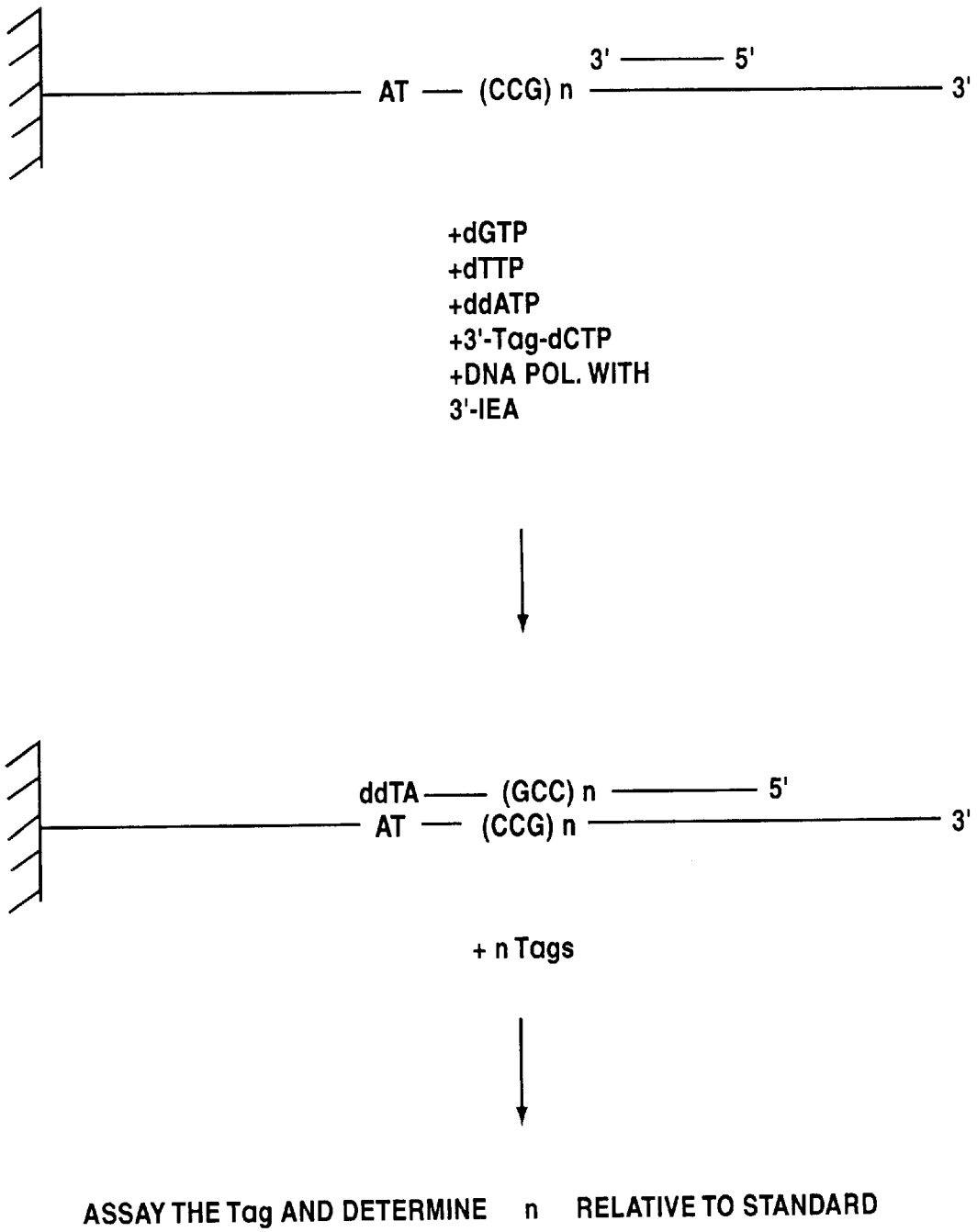

FIG. 5 Primers flanking the triplet repeat region are used to produce a PCR product that can be immobilized on a solid support using standard methods such as the Biotin-streptavidin system and magnetic beads (e.g. from Dynal).

Figure 6:
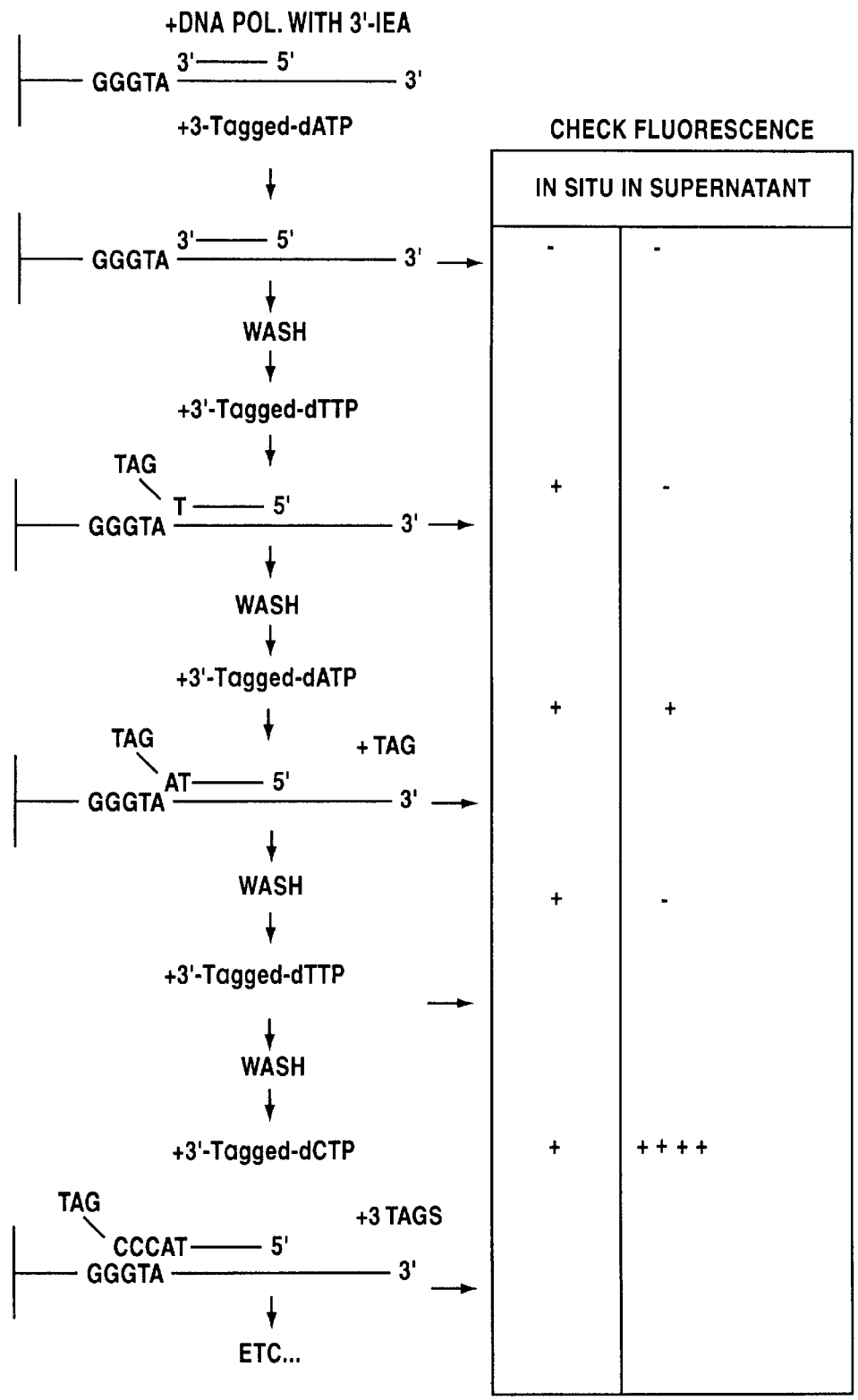

FIG. 6 Determination of the nucleotide sequence of an unknown DNA sample using a tag replacement scheme medicated by the 3'-IEA of DNA polymerase. The primed DNA is incubated sequentially with only one 3'-tagged-dNTP at a time, and incorporation is checked both in situ (e.g. by fluorimetric detection if the tag is fluorescent) and in the supernatant (see example 3).

In the following it is illustrated how to control the 3'-IEA, or on the other hand how to take advantage of the 3 TEA as described above.

Figure 4A:
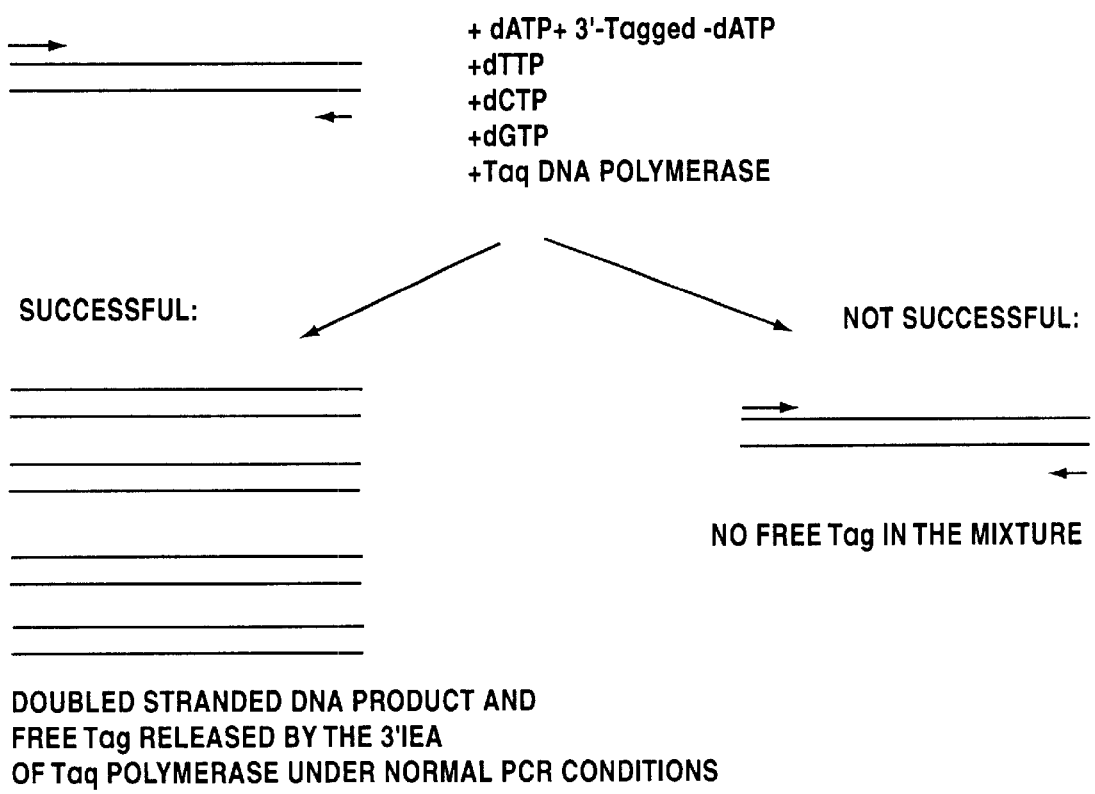

How to use a DNA polymerase (5 units) and four 3'-tagged nucleotides-5'-triphosphate (1 mM) in a non gel-based sequencing scheme in order to determine the nucleotide of an unknown DNA strand (2 picomoles) which is immobilized on a solid support (Dynabead M-280, DYNAL) is shown in FIG. 3, panel a). It is clear that the DNA polymerase must be devoid of 3'-IEA under these reaction conditions, otherwise the 3'-tagged-dNTPs would act as false chain terminators and make a correct and specific insertion of one nucleotide impossible. FIG. 4a shows that Taq polymerase is able to perform what is depicted in FIG. 3, but if care is taken to alter the classical reaction conditions of the Taq polymerase (72° C. pH 8.3, 1–5 mM $Mg^{2+}$) in order to fully inhibit its 3'-IEA (30°–45° C. pH 7.5, 1 mM $Mn^{2+}$, 5 mM citrate, 1 mM of each 3'-tagged nucleotides).

Figure 1:
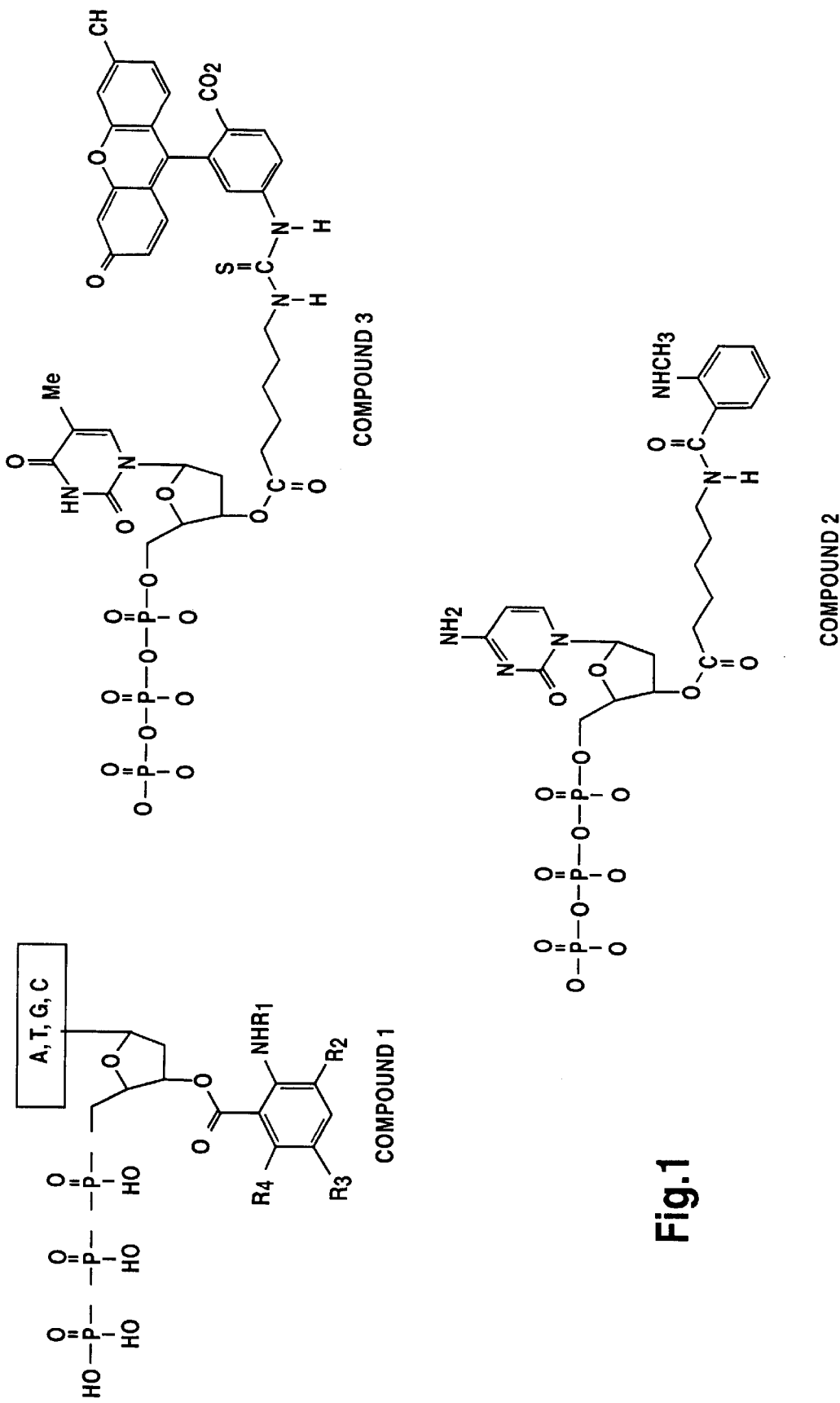
FIG. 1 Structures of several 2'-deoxy-3'-modified nucleotide 5'-triphosphates substrates. Those compounds were synthesized by Canard and Sarfti, Gene 148 (1994), 1–16, and are suitable as substrates for several DNA polymerases.

FIG. 3 panel b) shows how this sequencing scheme can be adapted to a very large number of DNA samples immobilized on a solid support, such as the one described by Fodor, 1994, and the incorporation scores recorded by an image analysis system (CCD camera). Same experimental conditions than FIG. 3a) are used, except that the chip carrying the immobilized DNAs is dipped into a reaction mixture containing only one 3'-tagged nucleotide at a time together with the 3'-IEA-devoid DNA polymerase in appropriate buffer, rinsed in washing buffer, analysed by means of a CCD camera, the coordinates of the DNA samples having incorporated the 3'-tagged nucleotide recorded, and the process reiterated in turn for the three remaining 3'-tagged nucleotides. After the four 3'-tagged nucleotides have been incorporated, all DNA samples are labelled with the tag. All the tags are removed with a deprotection solution, and the process is reiterated to determine which second base each DNA sample is able to incorporate. Again, it is clear that a DNA polymerase exhibiting 3'-IEA activity would completely fill the DNA strands as shown in FIG. 1a), invalidating the method.

The Following Examples Further Specify the Present Invention

EXAMPLE 1

The use of the 3'-IEA as a Marker of Nucleotide Incorporation into DNA.

Determining the success of an incorporation reaction (e.g., a PCR) is currently achieved by analysing the reaction products by means of agarose or polyacrylamide gel electrophoresis. Although simple, this step can be extremely tedious and poorly amenable to automation if a large number of PCR products are analysed at the same time. Thus, it would prove very useful to be able to check visually for incorporation of dNTPs, or at least circumvent the gel electrophoresis by use of an automatable incorporation test. The use of 3'-tagged dNTPs in conjunction with classical dNTPs and a DNA polymerase exhibiting 3'-IEA efficiently allows to decide whether or not nucleotides have been incorporated during a polymerization reaction. FIG. 4) illustrates the method where a small concentration of a 3'-tagged dNTP is included into a PCR together with a classical PCR mix (dNTPs, primers, DNA template and buffer).

Figure 4B:
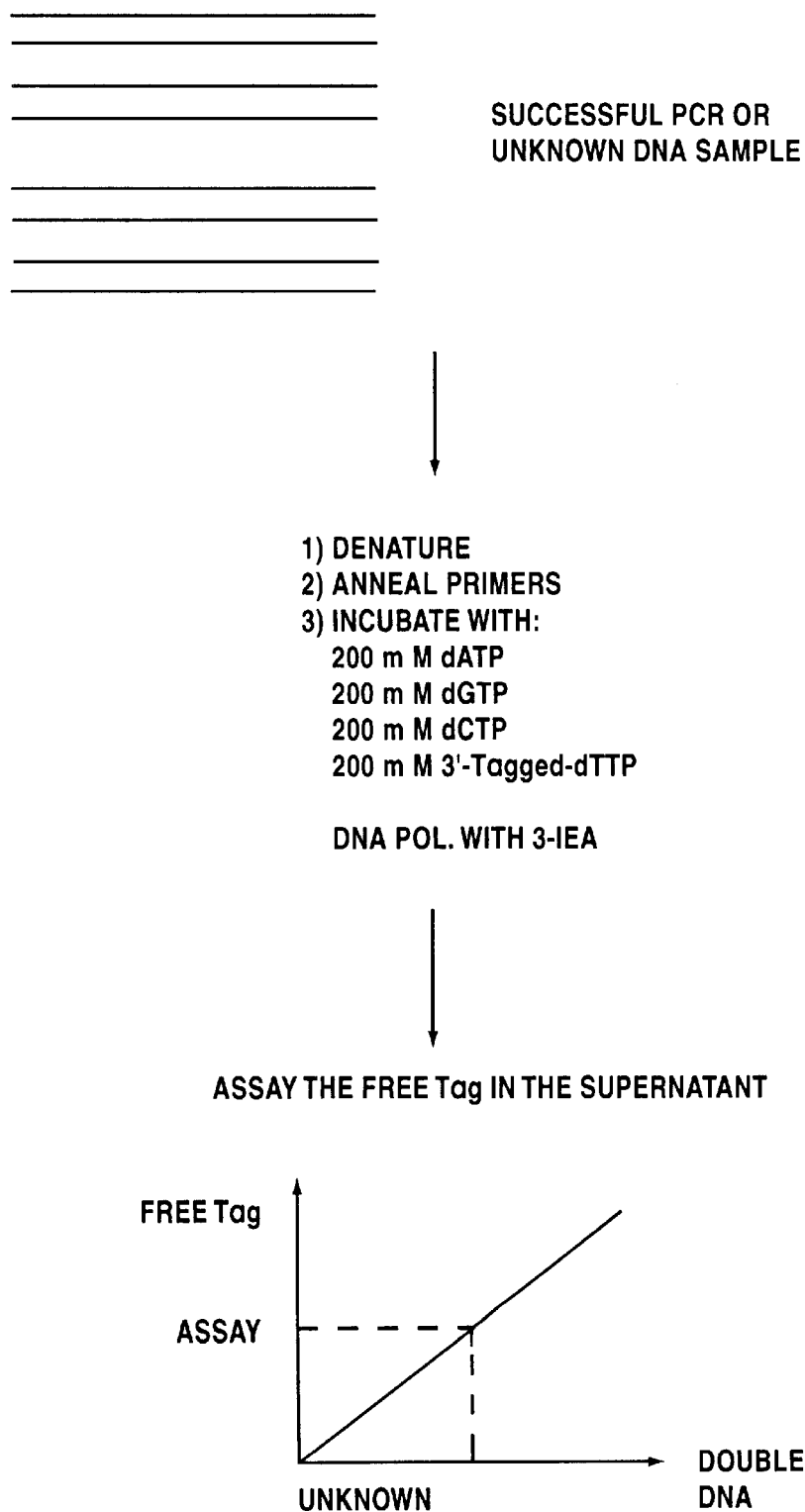

Because the 3'-tagged dNTP is inserted randomly in place of its normal 3'-OH-dNTP counterpart in front of its Watson-Crick cognate, and the tag is subsequently removed when addition of the next nucleotide occurs, the presence of an uncoupled tag in the supernatant is indicative that polymerization has occurred, the concentration of the tag in the supernatant being directly related to the number of inserted 3'-tagged nucleotides. FIG. 4b) illustrates a way of assaying the concentration of the double-stranded product when the PCR is completed. A mixture of three dNTP and a 3'-tagged dNTP is added to the PCR, and only one PCR cycle is performed taking care of the added DNA polymerase temperature of optimum activity. Again, the concentration of the double stranded DNA product is related to the free 3'-tag concentration in the supernatant. One can then select those PCR where incorporation has occurred, and analyse only those for correct product length using gel electrophoresis.

It is also apparent that this method can be used to determine a DNA concentration in an unknown DNA sample. Indeed, in the case of FIG. 4b, it is clear that the amount of released tag is proportional to the amount of template DNA, and that appropriate calibration with standards whose concentration is known allows to determine the DNA concentration of the said unknown sample by directly assaying the free tag in the supernatant. As stated before, the tag will be easily identified in its free form compared to its 3'-coupled form. For that purpose, best fluorophores are those that have a large Stockes shift, in such a wave that the maximum emission wavelength corresponding to their free form overlaps as few a possible with the maximum emission wavelength of their coupled form. This property can be advantageously used in order to obtain a fluorescent signal only once a free tag exists in the supernatant subsequent to expression of the 3'-IEA.

EXAMPLE 2

Counting the number of tri-nucleotide repeats in a given DNA sequence using a single tube and reaction: the case of CGG repeats and the fragile X syndrome.

The fragile X syndrome is the most frequent inherited mental retardation in humans (reviewed by Oostra et al, 1993). The molecular basis of the disease is a so-called "dynamic mutation" at the FMR1 locus involving rapid expansion of a (CGG)n triplet repeat whose number n is tightly correlated to normal, carrier, or pathologic phenotypes (Fu et al, 1991). Normal phenotypes have polymorphic (CGG) repeats ranging from 6 to 23 units, while carrier females have between 43 and 200 units. Affected individuals have more than 200 units of the CGG repeat. Hence, it is apparent that precise counting of the number of CGG repeats is clinically relevant at the diagnostic as well as the predictive level, and this can be just grossly estimated by classical cytogenetic methods or DNA analysis using PCR and subsequent gel electrophoresis. The use of 3'-IEA can advantageously substitute for the gel electrophoresis step and give a precise number of repeats in a very simple assay. Primers flanking the triplet repeat region (FIG. 5) are used to produce a PCR product that can be immobilized on a solid support using standard methods such as the Biotin-streptavidin system and magnetic beads (Dynal, Norway). A single-stranded DNA sequencing template is prepared by melting the duplex with NaOH as recommended by the manufacturer, and a primer is positioned immediately upstream of the (CGG)n region. Then, the primed DNA is incubated with a mixture containing a DNA polymerase exhibiting 3'-IEA, 200 μM dGTP, 50 μM of dATP and 50 μM ddTTP, and 400 μM 3'-tagged-dCTP, under conditions of pH, temperature and time optimum for both polymerization and 3'-IEA activities. The 2'3' dideoxynucleotide is incorporated only outside the CGG region and stop the reaction by DNA chain termination when it encounters its cognate base. Inside the CGG region, dGTP is incorporated in front of its cognate dC base, and 3'-tagged dCTP is incorporated also in the CGG region, and its 3'-tag removed during expression of the 3'-IEA. After the completion of the extension reaction, the supernatant is analysed for the presence of the free tag either directly, or after a brief purification procedure aimed at separating the free tag from the unincorporated 3'-tagged-dCTP, such as HPLC or a quick ion-exchange chromatography able to remove triphosphates compounds but not the free tag. The same experiment is run with a control DNA in which the CGG region has been fully characterized by DNA sequencing and comparison of the free tag concentration between the two samples allows to determine precisely the value of the CGG repeat number n taking into consideration the number of amplified alleles since the FMR1 region is located on the X chromosome.

It is clear that this technique can be applied to any other DNA sequence bearing a mono, di, tri nucleotide repeat, or longer sequences containing only 3 out of the four classical bases A, T, G and C, such as, for example, the repeated telomeric sequences (TTAGGG)n in which n has a biological significance. The composition of the ddNTP, dNTP, and 3'-tagged-dNTP mixture is easily adapted to the case under study to conveniently determine the number n of repeats of a given short sequence.

EXAMPLE 3

Determination of the nucleotide sequence of an unknown DNA sample using a tag replacement scheme mediated by the 3'-IEA of DNA polymerase.

The same experimental set-up than for FIG. 5 is used for the primer: template, but the aim of the experiment is to determine the unknown DNA nucleotide sequence of the template. The primed DNA is incubated sequentially with only one 3'-tagged-dNTP at a time, and incorporation is checked both in situ (e.g. by fluorimetric detection if the tag is fluorescent) and in the supernatant. Indeed, when the DNA polymerase exhibits its 3'-IEA, the attached tag at the 3'-end is released in the supernatant while the DNA is terminated by a new incoming nucleotide that has a 3'-tag, and thus, fluorescence must be determined at the 3'-end of the DNA chain and in the supernatant as a free tag. Basically, one 3'-tagged-dNTP is incubated at a time on the primed DNA. On FIG. 6, the order is the following: A, T, C, G all bearing a 3'-tag. Thus, 3'-tagged-dATP is added first, and fluorescence is checked in situ and in the supernatant. Both remain negative because an A is found in the template just adjacent to the primer. Then, 3'-tagged-dTTP is used and found incorporated by fluorimetric detection in situ only. A positive fluorescent signal in situ only indicates that no 3'-IEA has been expressed, and thus that only one T has been incorporated. After any (in situ or in supernatant) positive signal has been found, the sequential order of A, T, C and G-3'-tagged nucleotides is used again, and thus the mixture probed with 3'-tagged dATP, which is positive in our example because the next base is T. Fluorescence is detected both in situ and in the supernatant, indicating expression of 3'-IEA. In this case, it is important to know how many as have been inserted in a row. This can be easily achieved by adding to the supernatant an internal fluorimetric standard, that is, a known quantity of free tag in order to precisely estimate how many tags per template have been released by the 3'-IEA, in this case, only one.

This is illustrated for the next incorporated base, where four 3'-tagged dCTP are added in a row, releasing four free tags per template. These are assayed adding an internal standard in the supernatant, and subsequently fluorimetrically quantified. Although the process is easily done by hand, it is clear that a fluorescence detection system coupled to a computer can drive a robotic workstation that edits sequencing data in real-time as well as deduce which base to add according to the presence or absence of the tag in the 3'-end of the DNA or as a free tag in the supernatant. These ordered and logic steps are re-iterated for each base of the template until a complete DNA sequence is determined.

References

Canard, B. and Sarfati, S. R.:
Nouveaux derives utilisables en sequencage d'acides nucleiques (1993) patent FR9303538
Canard, B. and Sarfati, S. R.:
DNA polymerase fluorescent substrates with 3'-reversible tags.
Gene 148 (1994), 1–16
Canard, B. Cardona, B. and Sarfati, S. R.:
Novel Editing Activity of DNA Polymerases. (1994b) submitted for publication.
Davis, L. Fairfield. F. R., Harger. C. A., Jett. J. H., Keller, R. A., Hahn. J. H., Kratowski, L. A., Marropne, B. L., Martin. J. C., Nutter. H. L., Ratcliff. R. L., Shera, B. E., Simpson. D. J. and Soper, S. A.:
Rapid DNA Sequencing based upon single molecule detection.
Genetic Analysis Techniques and Applications 8 (1991), 1–7
Driscoll, R. J., Youngquist, M. G. and Baldeschwieler, J. D.:
Atomic-scale imaging of DNA using scanning tunelling microscopy.
Nature 346 (1990), 294–296
Fodor, S.:

Putting Genes on a Chip.
Science 264 (1994), 1400
Fu, Y. -H., Kuhl, D. P. A., Pizzuti A., Pieretti, M., Sutcliff, J., Richards, S., Verkerk, A. J. M. H., Holden, J. J. A., Fenwick, R. G., Warren, S. T., Oostra, B. A., Nelson. D. L. and Caskey, C. T.:
Variation of the CGG repeat at the fragile X site results in genetic instabilitiy: resolution of the Sherman paradox.
Cell 67 (1991), 1047–1058
Gibbs, R., Civitello, A., Burgess, K., Raghavachari, R., Metzker, M.:
Method and device for rapid DNA or RNA sequencing determination by a base addition scheme (1993) patent WO93/0518
Hultman, T., Bergh, S., Moks, T. and Ulhén, M.:
Bidirectional solid-phase sequencing of in vitro-amplified plasmid DNA.
Biotechniques 10 (1991), 84–93
Kornberg, A.:
DNA replication
(1980) Freeman, San Francisco
Kraevsky, A. A.:
Molecular Biology 21 (1987), 25–29
Mathies, R. A. and Huang, X. C.:
Capillary array electrophoresis: an approach to high-speed, high-throughput DNA sequencing.
Nature 359 (1992), 167–169
Maxam, A. M. and Gilbert, W.:
A new method for sequencing DNA.
Proc. Natl. Acad. Sci. USA 74 (1977), 560–564
Metzker, M., Raghavachari, R., Burgess, K. and Gibbs R.:
Stop-Start DNA synthesis in the base Addition Sequencing Scheme (BASS). (1994) abstract presented at Cold Spring Harbor Laboratory, "Genome Mapping and Sequencing" meeting, p 170.
Oostra, B. A., Willems, P. J. and Verkerk, A. J. M. H.:
Fragile X syndrome: a growing gene.
In Genome Analysis: Genome Mapping and Neurological Disorders (1993), Vol. 6, K. E. Davies and S. M. Tilghman, eds. (Cold Spring Harbor, N.Y.: Cold Spring Harbor Laboratorv Press), 45–75
Prober, J. M., Trainor, G. L., Dam, R. J. Hobbs, F. W., Robertson, C. W., Zagursky, R. J., Cocuzza, A. J., Jensen, M. A. and Baumeister, K.:
A system for rapid DNA sequencing with fluorescent chain-terminating dideoxynucleotides.
Science 238 (1987), 336–341
Sanger, F., Nicklen, S. and Coulson, A. R.:
DNA sequencing with chain-terminating inhibitors.
Proc. Natl. Acad. Sci. USA 74 (1977), 5463–5467
Sarfati, R S., Kansal, V. K. Munier, H., Glaser, P., Gilles, A. M., Labruyère, E., Mock, M., Danchin, A. and Barzu, O.:
Binding of 3'-anthraniloyl-2'deoxy-ATP to calmodulin-activated adenylate cyclase from *Bordetella pertussis* and *Bacillus anthracis*.
J. Biol. Chem. 265 (1990), 18902–18905
Strezoska, Z., Paunescu, T., Radosalvjevic, D., Labat, I., Drmanac, R. and Crkvenjakov, R.:
DNA sequencing by hybridization: 100 bases read by a non-gel-based method.
Proc. Natl. Acad. Sci USA 88 (1991), 10089–10093
Tabor, S. and Richardson, C.:
Effect of manganese ions on the incorporation of dideoxy-nucleotides by bacteriophage T7 DNA polymerase and *Escherichia coli* DNA polymerase.
I. Proc. Natl. Acad. Sci. USA 86 (1989), 4076–4080

Tsien, R.:
DNA Sequencing (1991), patent WO91/06678
Venter, C. J., Adams, M. D., Martin-gallardo, A., McCombie, R. W. and Fields, C.:
Genome sequence analysis: scientific objectives and practical strategies.
T.I.B.S. 10 (1992), 8–11

We claim:

1. A method for determining the incorporation of at least one tagged dNTP into a double-stranded DNA product, comprising:
   (a) providing, in a reaction vessel, a reaction solution comprising
      (i) a DNA template,
      (ii) at least one primer,
      (iii) a plurality of nucleotides comprising a plurality of dATP nucleotides, dTTP nucleotides, dCTP nucleotides and dGTP nucleotides, or analogues thereof, and at least one tagged dNTP of formula I, or an analogue thereof

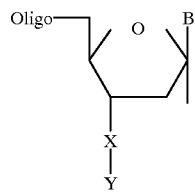

(I)

wherein:
      X is a bifunctional linkage group,
      Y is an activated group,
      B is selected from the group consisting of a purine, a pyrimidine, a deazapurine and a deazapyrimidine, and
   (iv) a thermophilic DNA polymerase which exhibits 3'-intrinsic editing activity;
   (b) synthesizing, in the reaction solution, a double-stranded DNA product in a polymerase chain reaction by sequentially adding to the at least one primer a plurality of nucleotides from step (a) which are complementary to the DNA template, the synthesizing step including incorporating the at least one tagged dNTP into the double-stranded DNA product and releasing the activated group from the at least one tagged dNTP concomitant to attaching to the at least one tagged dNTP one of the plurality of nucleotides from step (a) which is complementary to the DNA template, wherein said releasing step is effected by the DNA polymerase and is not effected by an additional enzyme, by radiation, or by an additional chemical; and
   (c) detecting the released activated group.

2. The method of claim 1, wherein X is selected from the group consisting of oxygen, sulfur and a —NH-group.

3. The method of claim 1, wherein Y is selected from the group consisting of —C(O)R, —CH$_2$—R, —C(S)NH—R and —C(O)NH—R, wherein R is selected from the group consisting of a hapten, a dye, a chromophore and a branched or unbranched alkyl group.

4. The method of claim 3, wherein R is at least one of a fluorescent chromophore and a $C_1$–$C_{20}$ alkyl group.

5. A method of determining an amount of tagged dNTPs incorporated into a double-stranded DNA product, comprising:

(a) providing, in a reaction vessel, a reaction solution comprising
  (i) a DNA template,
  (ii) at least one primer,
  (iii) a plurality of nucleotides comprising (1) three different non-tagged dNTPs, or analogues thereof, wherein each of the three different non-tagged dNTPs or an analogue thereof comprises a different one of the four DNA nucleotide bases, and (2) a plurality of tagged dNTPs of formula I, or analogues thereof,

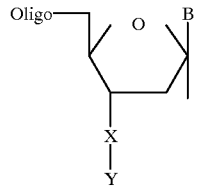

(I)

wherein:
  X is a bifunctional linkage group,
  Y is an activated group,
  B is selected from the group consisting of a purine, a pyrimidine, a deazapurine and a deazapyrimidine, wherein B is a DNA nucleotide base which is different from each of the three different non-tagged dNTPs or an analogue thereof,
  (iv) a thermophilic DNA polymerase which exhibits 3'-intrinsic editing activity; and
  (v) a suitable buffer;
(b) synthesizing, in the reaction solution, a double-stranded DNA product in a polymerase chain reaction by sequentially adding to the at least one primer a plurality of nucleotides from step (a) which are complementary to the DNA template, the synthesizing step including incorporating a plurality of tagged dNTPs into the double-stranded DNA product and releasing the activated group from each of the plurality of tagged dNTPs concomitant to attaching to each of the incorporated tagged dNTPs one of the plurality of nucleotides from step (a) which is complementary to the DNA template, wherein said releasing step is effected by the DNA polymerase and is not effected by an additional enzyme, by radiation, or by an additional chemical;
(c) determining the concentration of the released activated group in the reaction solution; and
(d) relating the concentration of the released activated group to the amount of tagged dNTPs incorporated into the double-stranded DNA product.

6. The method of claim 5, wherein X is selected from the group consisting of oxygen, sulfur and a —NH-group.

7. The method of claim 5, wherein Y is selected from the group consisting of —C(O)R, —CH$_2$—R, —C(S)NH—R and —C(O)NH—R, wherein R is selected from the group consisting of a hapten, a dye, a chromophore and a branched or unbranched alkyl group.

8. The method of claim 7, wherein R is at least one of a fluorescent chromophore and a C$_1$–C$_{20}$ alkyl group.

9. A method of calculating an amount of repeating sequences in a repeating region of a DNA sequence, wherein each repeating sequence comprises one, two or three of the four DNA nucleotide bases, the method comprising:

(a) hybridizing a primer with a DNA sequence comprising a repeating region comprising a plurality of repeating sequences, wherein each repeating sequence comprises one, two or three of the four DNA nucleotide bases to produce a primed DNA, wherein the primer flanks the repeating region;
(b) in a reaction vessel containing a reaction solution, combining the primed DNA with a plurality of nucleotides comprising
  (i) a first non-tagged dNTP, or analogue thereof,
  (ii) a second non-tagged dNTP, or analogue thereof,
  (iii) a non-tagged ddNTP, or analogue thereof,
  (iv) a tagged dNTP of formula I, or analogue thereof,

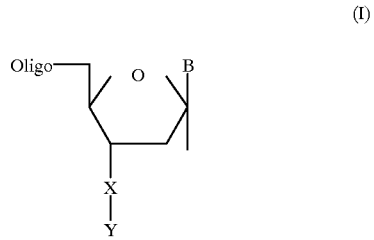

(I)

wherein:
  X is a bifunctional linkage group,
  Y is an activated group, and
  B is selected from the group consisting of a purine, a pyrimidine, a deazapurine and a deazapyrimidine,
  wherein each of (i), (ii), (iii) and (iv) comprises a different one of the four DNA nucleotide bases, and wherein the non-tagged ddNTP or analogue thereof is a DNA nucleotide base which is non-complementary to a DNA nucleotide base of the repeating sequence and the tagged dNTP or analogue thereof is complementary to a DNA nucleotide base of the repeating sequence, and
  (v) a thermophilic DNA polymerase which exhibits 3'-intrinsic editing activity;
(c) synthesizing, in the reaction solution, a double-stranded DNA product in a polymerase chain reaction by sequentially adding to the primer a plurality of nucleotides from step (b) which are complementary to the DNA sequence, the synthesizing step including incorporating a plurality of tagged dNTPs into the double-stranded DNA product and releasing the activated group from each of the plurality of tagged dNTPs concomitant to attaching to each of the incorporated tagged dNTPs one of the plurality of nucleotides from step (a) which is complementary to the DNA sequence wherein said releasing step is effected by the DNA polymerase and is not effected by an additional enzyme, by radiation, or by an additional chemical;
(d) terminating the synthesis of the double-stranded DNA product outside of the repeating region by incorporating the non-tagged ddNTP or analogue thereof into the double-stranded DNA product;
(e) determining the concentration of the released activated group in the reaction solution; and
(f) relating the concentration of the released activated group to the amount of repeating sequences in the repeating region of the DNA sequence.

10. The method of claim 9, wherein X is selected from the group consisting of oxygen, sulfur and a —NH-group.

11. The method of claim 9, wherein Y is selected from the group consisting of —C(O)R, —CH$_2$—R, —C(S)NH—R and —C(O)NH—R, wherein R is selected from the group consisting of a hapten, a dye, a chromophore and a branched or unbranched alkyl group.

12. The method of claim 11, wherein R is at least one of a fluorescent chromophore and a $C_1$–$C_{20}$ alkyl group.

13. A method of determining a nucleotide sequence of a DNA sample, comprising:
(a) hybridizing a primer with the DNA sample to produce a primed DNA, wherein the primer flanks the repeating region;
(b) attaching to the primed DNA a first tagged dNTP of formula I, or an analogue thereof, in the presence of a thermophilic DNA polymerase, which exhibits 3'-intrinsic editing activity, in a reaction vessel containing a reaction solution, wherein the first tagged dNTP is complementary to the DNA sample, to form a double-stranded DNA product,

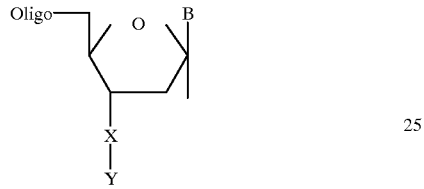

(I)

wherein:
X is a bifunctional linkage group,
Y is an activated group, and
B comprises one of the four DNA nucleotide bases;
(c) determining a nucleotide in the nucleotide sequence of the DNA sample by detecting the presence or absence of the activated group of the first tagged dNTP on the double-stranded DNA product and in the reaction solution;
(d) releasing the activated group of the first tagged dNTP by repeating, at least once, step (b) using a second tagged dNTP of formula I, or an analogue thereof, which is complementary to the DNA sample, wherein the activated group of the first tagged dNTP is released from the first tagged dNTP concomitant to attaching to the primed DNA the second tagged dNTP or analogue thereof, wherein said releasing step is effected by the DNA polymerase and is not effected by an additional enzyme, by radiation, or by an additional chemical; and
(e) determining the nucleotide sequence of the DNA sample, by detecting the presence or absence of the activated group of the first tagged dNTP and the activated group of the second tagged dNTP on the double-stranded DNA product and in the reaction solution.

14. The method of claim 13, wherein X is selected from the group consisting of oxygen, sulfur and a —NH-group.

15. The method of claim 13, wherein Y is selected from the group consisting of —C(O)R, —CH$_2$—R, —C(S)NH—R and —C(O)NH—R, wherein R is selected from the group consisting of a hapten, a dye, a chromophore and a branched or unbranched alkyl group.

16. The method of claim 15, wherein R is at least one of a fluorescent chromophore and a $C_1$–$C_{20}$ alkyl group.

17. A method of determining a nucleotide sequence of each of a plurality of DNA samples, the method comprising:
(a) providing a plurality of DNA samples immobilized on a solid support, wherein each DNA sample comprises a first strand having a nucleotide region which nucleotide sequence is to be determined and a second strand, having a primed end, flanking the nucleotide region;
(b) providing a plurality of nucleotides comprising
(i) a first tagged dNTP of formula I, or an analogue thereof,
(ii) a second tagged dNTP of formula I, or an analogue thereof,
(iii) a third tagged dNTP of formula I, or an analogue thereof, and
(iv) a fourth tagged dNTP of formula I, or an analogue thereof,

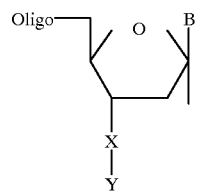

(I)

wherein:
X is a bifunctional linkage group,
Y is an activated group, and
B is selected from the group consisting of a purine, a pyrimidine, a deazapurine and a deazapyrimidine,
wherein each of (i), (ii), (iii) and (iv) comprises a different one of the four DNA nucleotide bases;
(c) attaching the first tagged dNTP or analogue thereof to the second strand of each DNA sample having a complementary nucleotide therewith on the first strand by combining, in a reaction vessel, the first tagged dNTP or analogue thereof, the plurality of DNA samples and a thermophilic DNA polymerase, wherein said attaching step is conducted at a temperature below the optimum temperature for the DNA polymerase activity;
(d) determining a nucleotide in the nucleotide sequence of each of the plurality of DNA samples to which the first tagged dNTP or analogue thereof has been attached in step (c), by detecting the attached activated group of the attached first tagged dNTP or analogue thereof,
(e) repeating steps (c)–(d) with the second tagged dNTP or analogue thereof,
(f) repeating steps (c)–(d) with the third tagged dNTP or analogue thereof,
(g) repeating steps (c)–(d) with the fourth tagged dNTP or analogue thereof,
(h) removing each of the activated groups on (i), (ii), (iii) and (iv), and
(i) repeating, at least once, steps (c)–(h) to determine the nucleotide sequence of each of the plurality of DNA samples.

18. The method of claim 17, wherein X is selected from the group consisting of oxygen, sulfur and a —NH-group.

19. The method of claim 17, wherein Y is selected from the group consisting of —C(O)R, —CH$_2$—R, —C(S)NH—R and —C(O)NH—R, wherein R is selected from the group consisting of a hapten, a dye, a chromophore and a branched or unbranched alkyl group.

20. The method of claim 19, wherein R is at least one of a fluorescent chromophore and a $C_1$–$C_{20}$ alkyl group.

21. The method of claim 17, wherein the activating groups are removed using a ribo- or desoxyribonucleotide-5'-triphosphate, or a derivative thereof.

22. A method of determining a nucleotide of a DNA sample, the method comprising:
(a) providing a DNA sample immobilized on a solid support, wherein the DNA sample comprises a first strand having a nucleotide which is to be determined and a second strand, having a primed end, flanking the nucleotide;
(b) providing a plurality of nucleotides comprising
  (i) a tagged dATP nucleotide of formula I, or an analogue thereof,
  (ii) a tagged dTTP nucleotide of formula I, or an analogue thereof,
  (iii) a tagged dCTP nucleotide of formula I, or an analogue thereof, and
  (iv) a tagged dGTP nucleotide of formula I, or an analogue thereof,

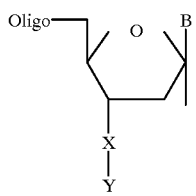

(I)

wherein:
X is a bifunctional linkage group,
Y is an activated group,
B is selected from the group consisting of a purine, a pyrimidine, a deazapurine and a deazapyrimidine,
wherein each of (i), (ii), (iii) and (iv) comprises a different activated group;
(c) attaching one of (i), (ii), (iii) and (iv), having a complementary nucleotide to the nucleotide which is to be determined, to the second strand of the DNA sample to produce a tagged DNA sample by combining, in a reaction vessel, the plurality of nucleotides, the DNA sample and a thermophilic DNA polymerase, wherein said attaching step is conducted at a temperature below the optimum temperature for the DNA polymerase activity; and
(d) determining the nucleotide of the tagged DNA sample by detecting the attached activated group of the attached tagged nucleotide or analogue thereof.

23. The method of claim 22, wherein X is selected from the group consisting of oxygen, sulfur and a —NH-group.

24. The method of claim 22, wherein Y is selected from the group consisting of —C(O)R, —CH$_2$—R, —C(S)NH—R and —C(O)NH—R, wherein R is selected from the group consisting of a hapten, a dye, a chromophore and a branched or unbranched alkyl group.

25. The method of claim 24, wherein R is at least one of a fluorescent chromophore and a $C_1$–$C_{20}$ alkyl group.

26. The method of claim 22, further comprising, after step (c), separating the tagged DNA sample and the plurality of nucleotides.

27. The method of claim 1, wherein the reaction solution is buffered.

* * * * *